(12) United States Patent
Schroeder (10) Patent No.: US 6,966,932 B1
(45) Date of Patent: Nov. 22, 2005

(54) COMPOSITE ACETABULAR COMPONENT

(75) Inventor: David Wayne Schroeder, Winona Lake, IN (US)

(73) Assignee: Biomet, Inc., Warsaw, IN (US)

(*) Notice: Subject to any disclaimer, the term of this patent is extended or adjusted under 35 U.S.C. 154(b) by 0 days.

(21) Appl. No.: 10/068,135

(22) Filed: Feb. 5, 2002

(51) Int. Cl.⁷ .............................................. A61F 2/32
(52) U.S. Cl. .................................................. 623/22.19
(58) Field of Search .................... 623/22.15, 22.17, 623/22.19, 22.2, 22.21, 22.24, 22.28, 22.29, 623/22.56

(56) References Cited

U.S. PATENT DOCUMENTS

| | | | |
|---|---|---|---|
| 2,668,531 A | | 2/1954 | Haboush |
| 3,806,960 A | | 4/1974 | Weber |
| 4,159,358 A | * | 6/1979 | Hench et al. ............... 427/318 |
| 4,164,794 A | * | 8/1979 | Spector et al. ............. 623/23.6 |
| 4,365,359 A | * | 12/1982 | Raab ........................... 606/76 |
| 4,778,474 A | | 10/1988 | Homsy |
| 4,812,120 A | * | 3/1989 | Flanagan et al. ............. 433/173 |
| 4,908,033 A | * | 3/1990 | Frey et al. ................... 623/22 |
| 4,936,855 A | * | 6/1990 | Sherman ...................... 623/22 |
| 5,037,442 A | * | 8/1991 | Wintermantel et al. .... 623/23.16 |
| 5,047,054 A | * | 9/1991 | Vijayan et al. ............. 623/23.6 |
| 5,049,158 A | * | 9/1991 | Engelhardt et al. ........... 623/22 |
| 5,061,286 A | * | 10/1991 | Lyle ........................... 623/23.63 |
| 5,314,492 A | * | 5/1994 | Hamilton et al. .......... 623/23.34 |
| 5,409,777 A | * | 4/1995 | Kennedy et al. ......... 428/411.1 |
| 5,480,448 A | * | 1/1996 | Mikhail .................... 623/22.24 |
| 5,507,826 A | * | 4/1996 | Besselink et al. ......... 623/22.29 |
| 5,549,700 A | | 8/1996 | Graham et al. |
| 5,730,922 A | * | 3/1998 | Babb et al. .................. 264/258 |
| 5,739,193 A | * | 4/1998 | Walpita et al. .............. 524/413 |
| 5,788,916 A | | 8/1998 | Caldarise |
| 5,800,555 A | * | 9/1998 | Gray, III ................... 623/22.29 |
| 5,879,404 A | | 3/1999 | Bateman et al. |
| 5,989,294 A | * | 11/1999 | Marlow ........................ 623/22 |
| 6,132,469 A | * | 10/2000 | Schroeder ................ 623/22.24 |
| 6,368,354 B2 | * | 4/2002 | Burstein et al. ......... 623/22.28 |
| 6,394,944 B1 | * | 5/2002 | Hyllberg et al. ............. 492/54 |
| 6,475,243 B1 | * | 11/2002 | Sheldon et al. .......... 623/22.28 |
| 6,610,097 B2 | * | 8/2003 | Serbousek et al. ....... 623/22.24 |
| 6,638,311 B2 | * | 10/2003 | Wang et al. .............. 623/22.32 |
| 2003/0175488 A1 | * | 9/2003 | Asthana et al. ............. 428/212 |

FOREIGN PATENT DOCUMENTS

| | | | | |
|---|---|---|---|---|
| FR | 2700686 A1 | * | 7/1994 | ............. A61F 2/34 |
| JP | 402161943 A | * | 6/1990 | ............. A61F 2/34 |

* cited by examiner

Primary Examiner—Kevin Shaver
Assistant Examiner—Anu Ramana
(74) Attorney, Agent, or Firm—Harness, Dickey & Pierce, P.L.C.

(57) ABSTRACT

Composite acetabular components, and methods of making and using same, are described. The composites consist of a ceramic liner having a backing of plastic material, such as but not limited to ultra high molecular weight polyethylene (UHMWPE), molded around the ceramic liner. The back surface of the ceramic liner is textured to enhance the mechanical bonding strength of the plastic backing to the textured ceramic liner during the molding process.

25 Claims, 7 Drawing Sheets

COMPOSITE ACETABULAR COMPONENT

FIELD OF THE INVENTION

The present invention relates generally to acetabular components, and more particularly to composite acetabular components having an inner ceramic insert and an outer ultrahigh molecular weight polyethylene (UHMWPE) backing bonded thereto, and methods of making same.

BACKGROUND OF THE INVENTION

The use of various prosthetic implant systems, such as those used for the total replacement of hips, has become increasingly more commonplace. For example, hip replacements are performed to alleviate conditions caused by osteoarthritis, rheumatoid arthritis, fractures, dislocations, congenital deformities, and other hip-related conditions.

Total hip arthroplasty involves replacing the damaged surfaces of the hip with artificial surfaces. Typically, the surgeon removes the head and neck of the femur and replaces them with a femoral component comprised of a metallic ball and stem. The damaged hip socket is lined with an acetabular component which is typically comprised of a metallic cup lined with a plastic material (such as polyethylene). The ball and stem fit into this cup, creating a new, movable hip joint.

Ceramic acetabular liners began to be used in the early 1970's with a monolithic design that was attached to the acetabulum, either with or without bone cement. In the early 1990's, modular ceramic liners were introduced that were seated into a metal shell via a taper connection. In the mid-1990's, ultrahigh molecular weight polyethylene (UHMWPE)-backed ceramic liners were introduced, which were then inserted into a metal shell. These ceramic liners were pressed into the UHMWPE backing. Some of these liners had anti-rotation grooves to enhance the locking strength of the ceramic liner to the UHMWPE backing. Surface texturing was difficult to impart on these ceramic liners as diamond tooling was typically required to grind or machine, and grit blasting methods, which can be used on metal, typically did not work on ceramic materials.

Therefore, there is a need for a composite acetabular component that has increased bonding strength between the ceramic liner and the UHMWPE backing in order to increase survivorship of the composite acetabular component.

SUMMARY OF THE INVENTION

In accordance with a first embodiment of the present invention, a composite acetabular component is provided, comprising: (1) a ceramic insert member having an inner surface and an outer surface; and (2) a thermoplastic backing member molded onto the outer surface of the ceramic insert member when the thermoplastic backing member is in a substantially softened state; wherein the outer surface of the ceramic insert is provided with a texture so as to increase the mechanical bonding between the thermoplastic backing member and the outer surface of the ceramic liner member.

In accordance with a second embodiment of the present invention, a composite acetabular component is provided, comprising: (1) a ceramic insert member, the ceramic insert member having a substantially hemispherical shape, the ceramic insert member having an inner surface and an outer surface; and (2) a thermoplastic backing member molded onto the outer surface of the ceramic insert member when the thermoplastic backing member is in a substantially softened state, the thermoplastic backing member having a substantially hemispherical shape, the thermoplastic backing member having an inner surface and an outer surface; wherein the outer surface of the ceramic insert is provided with a roughened texture so as to increase the mechanical bonding between the inner surface of the softened thermoplastic backing member and the roughened texture of the outer surface of the ceramic liner member.

In accordance with a third embodiment of the present invention, an acetabulum replacement system is provided, comprising: (1) an acetabulum member; (2) a composite acetabular component, comprising: (a) a ceramic insert member having an inner surface and an outer surface; and (b) a thermoplastic backing member molded onto the outer surface of the ceramic insert member when the thermoplastic backing member is in a substantially softened state; wherein the outer surface of the ceramic insert is provided with a texture so as to increase the mechanical bonding between the thermoplastic backing member and the outer surface of the ceramic liner member; and (3) a securing mechanism for securing the acetabulum member to the composite acetabular component.

In accordance with a fourth embodiment of the present invention, a hip replacement system is provided, comprising: (1) an acetabulum member; (2) a composite acetabular component, comprising: (a) a ceramic insert member having an inner surface and an outer surface; and (b) a thermoplastic backing member molded onto the outer surface of the ceramic insert member when the thermoplastic backing member is in a substantially softened state; wherein the outer surface of the ceramic insert is provided with a texture so as to increase the mechanical bonding between the thermoplastic backing member and the outer surface of the ceramic liner member; (3) a femoral component having a ball-shaped portion adapted to be received in the composite acetabular component; and (4) a securing mechanism for securing the acetabulum member to the composite acetabular component.

In accordance with a fifth embodiment of the present invention, a method of making a composite acetabular component is provided, comprising: (1) providing a ceramic insert member having an inner surface and an outer surface; (2) providing a thermoplastic material; (3) imparting a texture to the outer surface of the ceramic insert member; (4) softening the thermoplastic material; and (5) contacting the textured outer surface of the ceramic insert member with the softened thermoplastic material for a sufficient period of time to form a thermoplastic backing member onto the textured outer surface of the ceramic insert member; wherein the texture of the outer surface of the ceramic insert member increases the mechanical bonding between the thermoplastic backing member and the outer surface of the ceramic liner member.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

The same elements or parts throughout the figures are designated by the same reference of characters.

DETAILED DESCRIPTION OF THE PREFERRED EMBODIMENTS

The following description of the preferred embodiment(s) are merely exemplary in nature and are in no way intended to limit the invention, its application, or uses.

Figure 1:
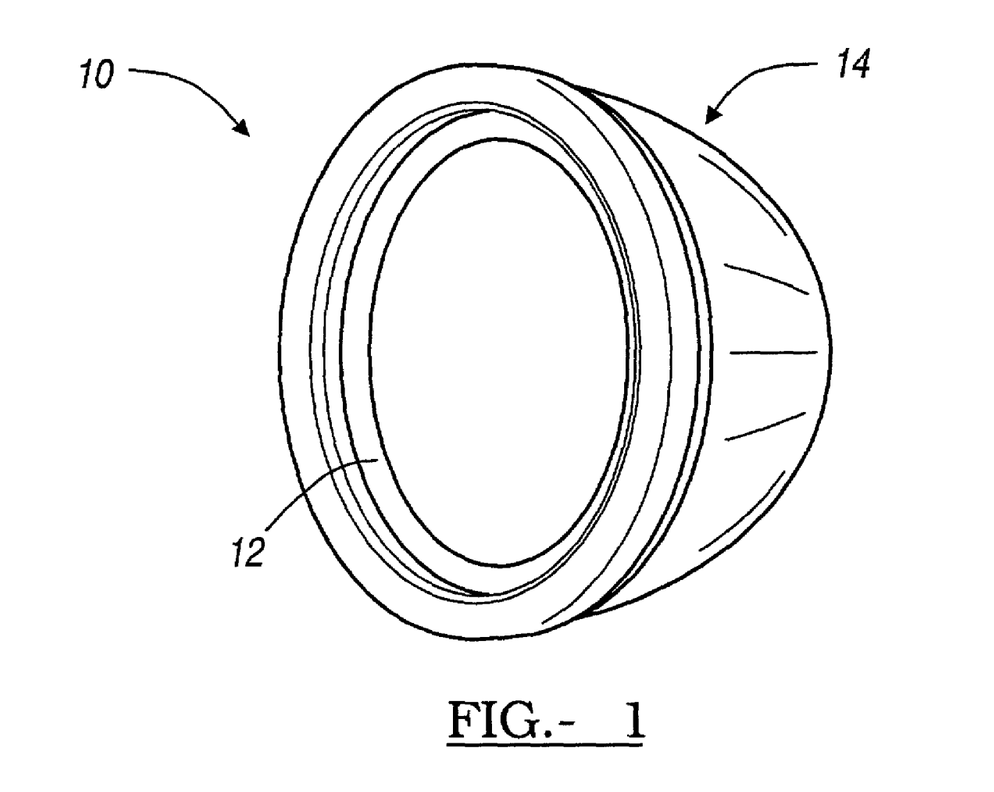
FIG. 1 illustrates a perspective view of a composite acetabular component, in accordance with the general teachings of the present invention.
Figure 2:
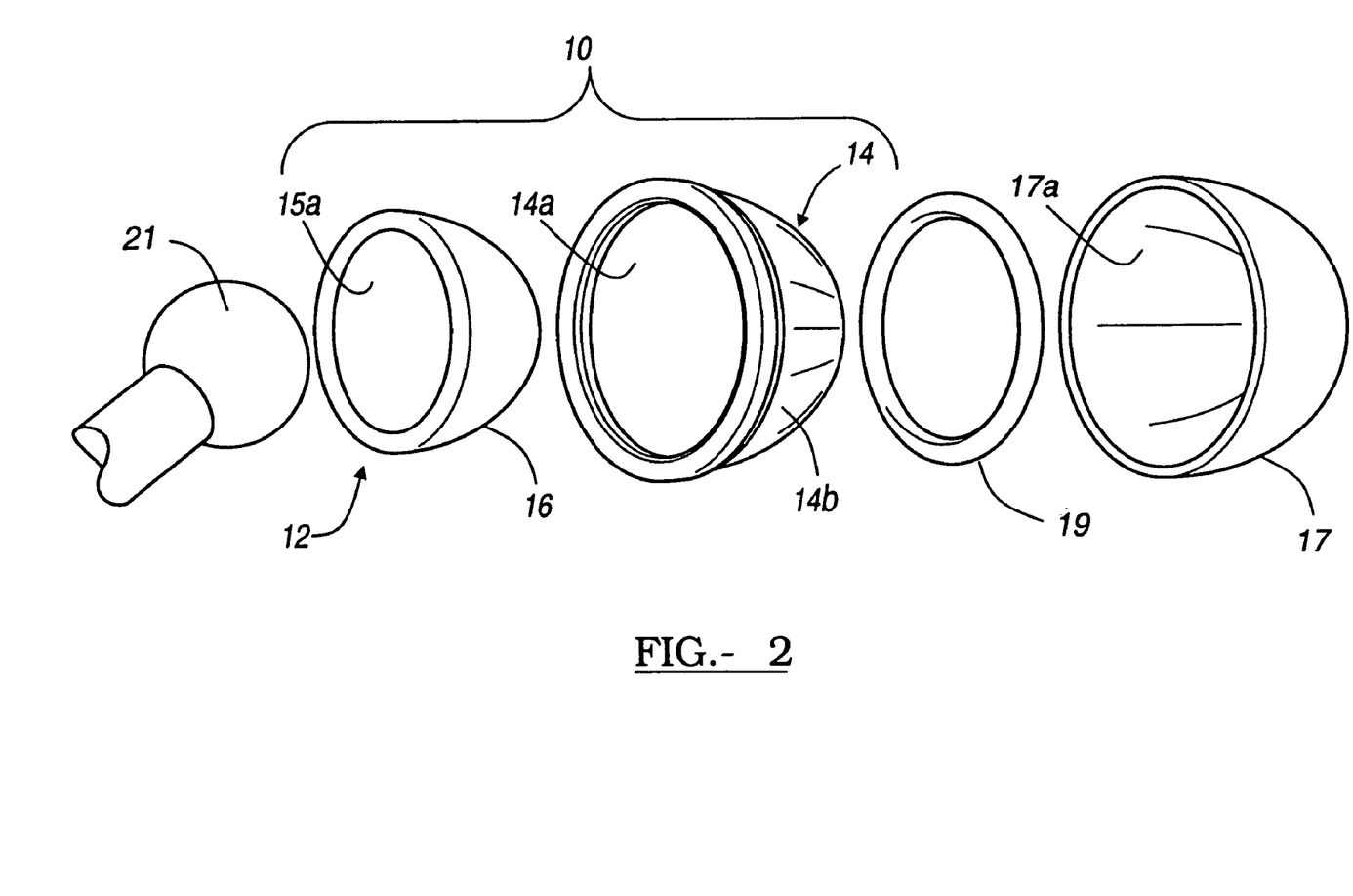
FIG. 2 illustrates an exploded view of a composite acetabular component as part of an acetabulum replacement system and a hip replacement system, in accordance with the general teachings of the present invention.
Figure 3:
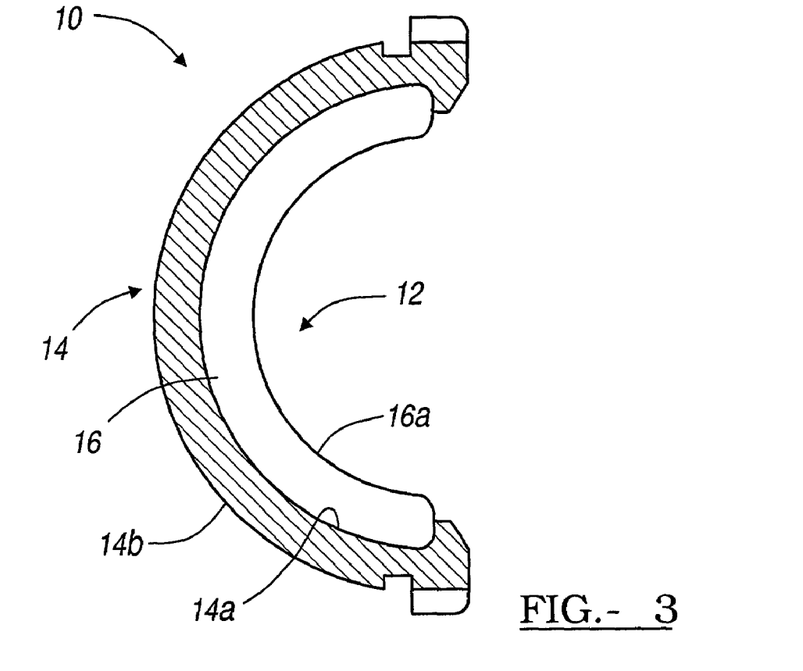
FIG. 3 illustrates a cross-sectional view of a composite acetabular component, in accordance with the general teachings of the present invention.

Referring to FIGS. 1–3, a modular acetabular component 10 includes a ceramic liner or insert 12 (having back surface 16 and inner surface 16a) having a thermoplastic backing 14 (having inner surface 14a and back surface 14b) molded onto the back surface 16 of the ceramic liner 12. Preferred thermoplastic materials can include, but are not limited to polyethylenes. Preferred polyethylenes can include, but are not limited to ultra high molecular weight polyethylene (UHMWPE). The modular acetabular component 10 is intended to cooperate with an inner surface 17a of an acetabulum member 17 and be secured thereto by a securing mechanism, such as a locking ring 19, as part of an acetabulum replacement system. Additionally, the ball portion 21 of a femoral component is intended to be received into the ceramic liner 12 in a rotational relationship therewith, as part of a hip replacement system.

Figure 4:
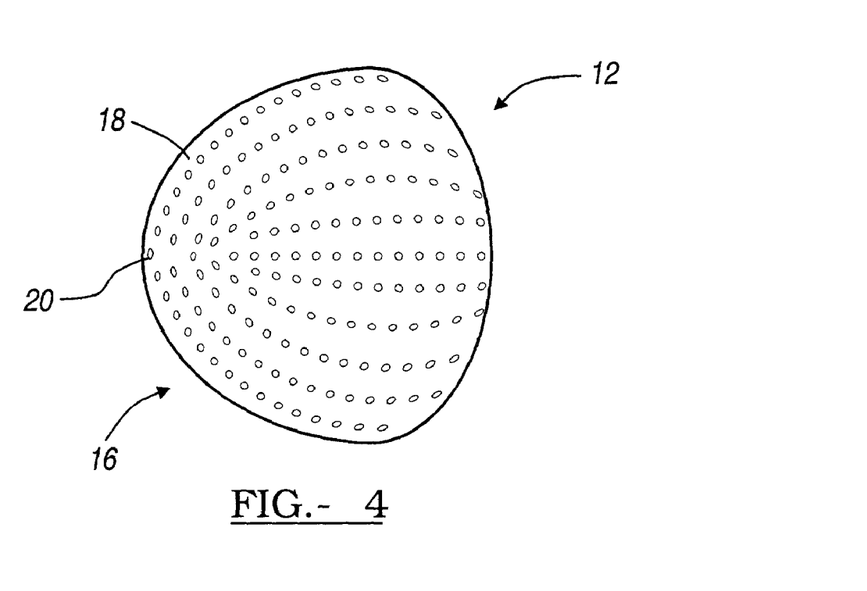
FIG. 4 illustrates a rear perspective view of the micro-roughness on the back surface of a ceramic liner of the composite acetabular component, in accordance with the general teachings of the present invention.
Figure 5:
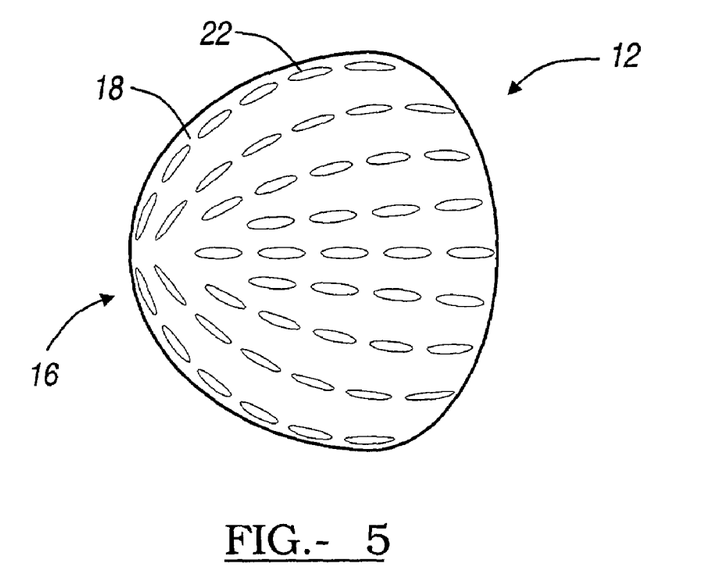
FIG. 5 illustrates a rear perspective view of the surface depressions on the back surface of a ceramic liner of the composite acetabular component, in accordance with the general teachings of the present invention.
Figure 6:
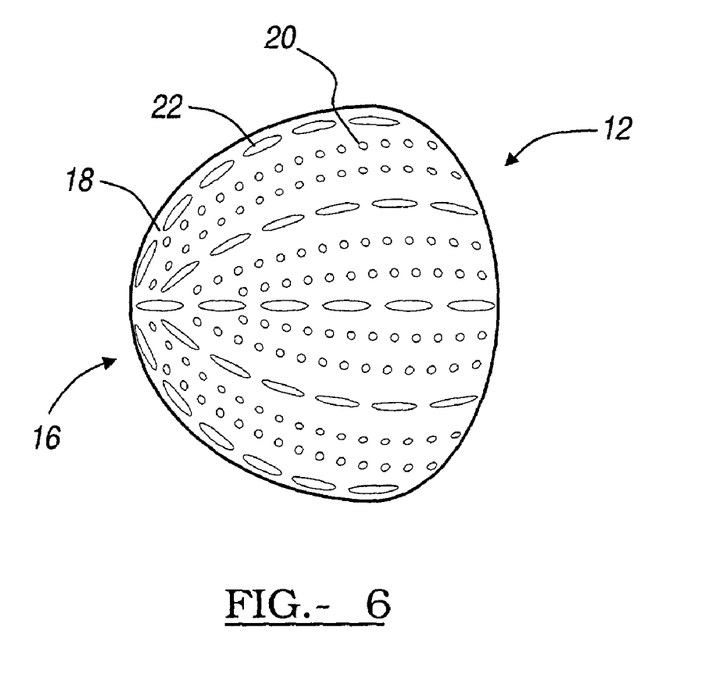
FIG. 6 illustrates a rear perspective view of the micro-roughness and surface depressions on the back surface of a ceramic liner of the composite acetabular component, in accordance with the general teachings of the present invention.
Figure 7:
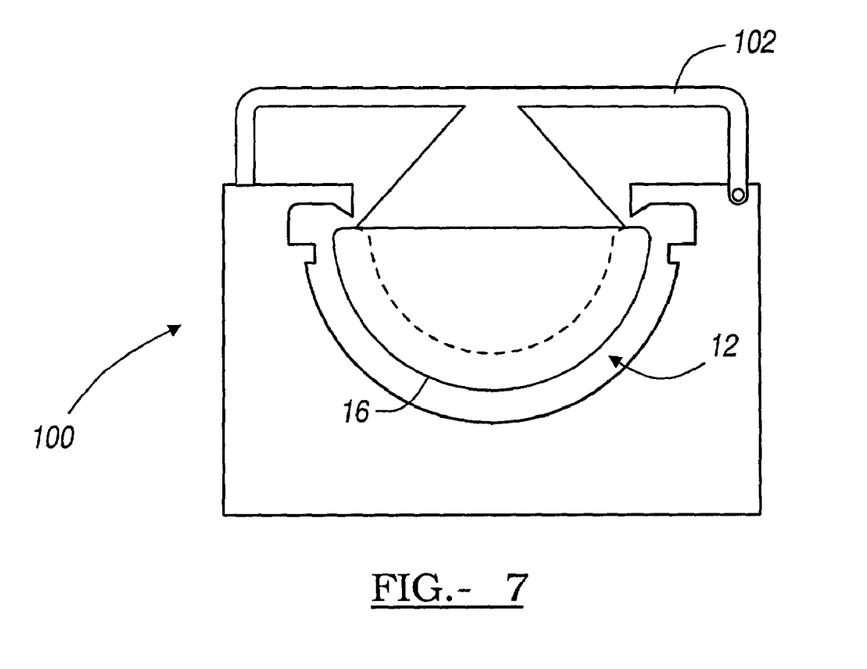
FIG. 7 illustrates a schematic view of an illustrative apparatus for molding a thermoplastic backing onto the ceramic liner of the composite acetabular component, in accordance with the general teachings of the present invention.
Figure 8:
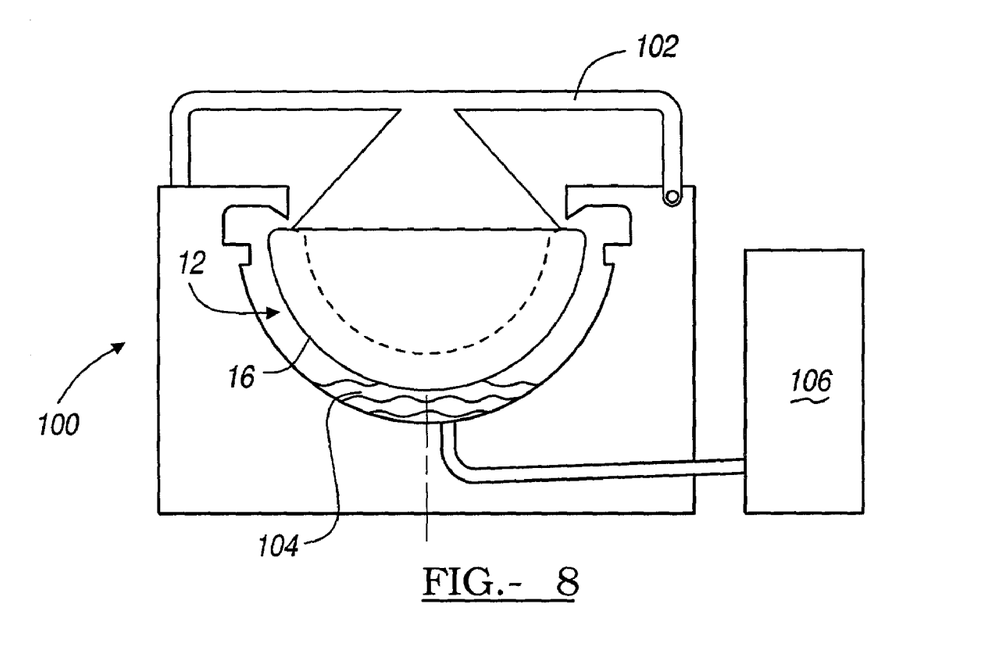
FIG. 8 illustrates a schematic view of a softened thermoplastic material being introduced into the illustrative apparatus for molding a thermoplastic backing onto the ceramic liner of the composite acetabular component, in accordance with the general teachings of the present invention.
Figure 9:
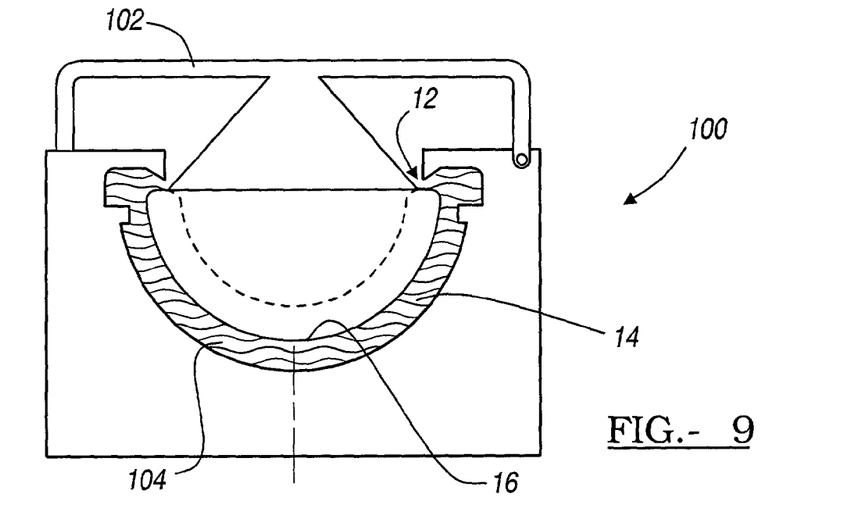
FIG. 9 illustrates a schematic view of the softened thermoplastic material forming a backing onto the ceramic liner of the composite acetabular component, in accordance with the general teachings of the present invention.
Figure 10:
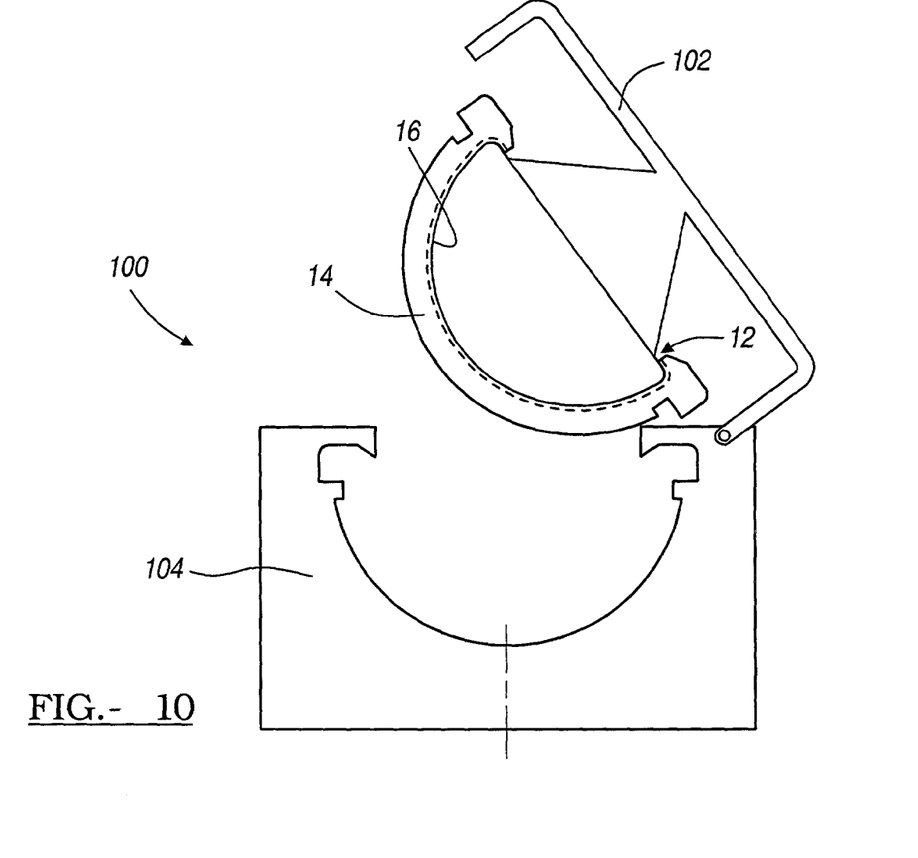
FIG. 10 illustrates a schematic view of the completed composite acetabular component being removed from the illustrative apparatus for molding a thermoplastic backing onto the ceramic liner of the composite acetabular component, in accordance with the general teachings of the present invention.

Referring to FIGS. 4–6, in order to increase the mechanical bonding, mechanical interdigitation and/or bonding strength between the ceramic insert 12 and the thermoplastic backing 14, it is first necessary to impart a surface texture 18 onto the back surface 16 of the ceramic liner 12 prior to bonding with the thermoplastic backing 14.

The surface texture 18 preferably has a certain degree of roughness associated therewith. In accordance with a preferred embodiment, the surface texture 18 has an arithmetical mean roughness (Ra) in the range of about 5 to about 10 microns. In accordance with still another preferred embodiment, the surface texture 18 has a ten-point mean roughness (Rz) in the range of about 50 to about 75 microns. This micro-roughness 20 is intended to aid in increasing the mechanical bonding, mechanical interdigitation and/or bonding strength between the two components.

Alternatively, surface features such as but not limited to macro-grooves 22 (i.e., longer and/or deeper surface depressions), can also be imparted onto the back surface 16 of the ceramic liner 12. Furthermore, a combination of surface features including but not limited to micro-roughness 20 and macro-grooves 22 can be imparted onto the back surface 16 of the ceramic liner 12.

The surface texture 18 can be imparted in accordance with any number of conventional methods, including but not limited to ultrasonic machining. Alternatively, the surface texture 18 can be imparted onto the back surface 16 of the ceramic liner 12 while in the green state, i.e., prior to being sintered.

Referring to FIGS. 7–10, an illustrative example of a method for making the composite acetabular component 10 will be described.

The ceramic liner 12 is preferably inserted into a two part mold tool 100 and held in place with any suitable fixturing device 102 so as to expose the back surface 16 of the ceramic liner 12. Preferably the mold tool 100 has a configuration shaped to permit the formation of the thermoplastic backing 14.

Figure 11:
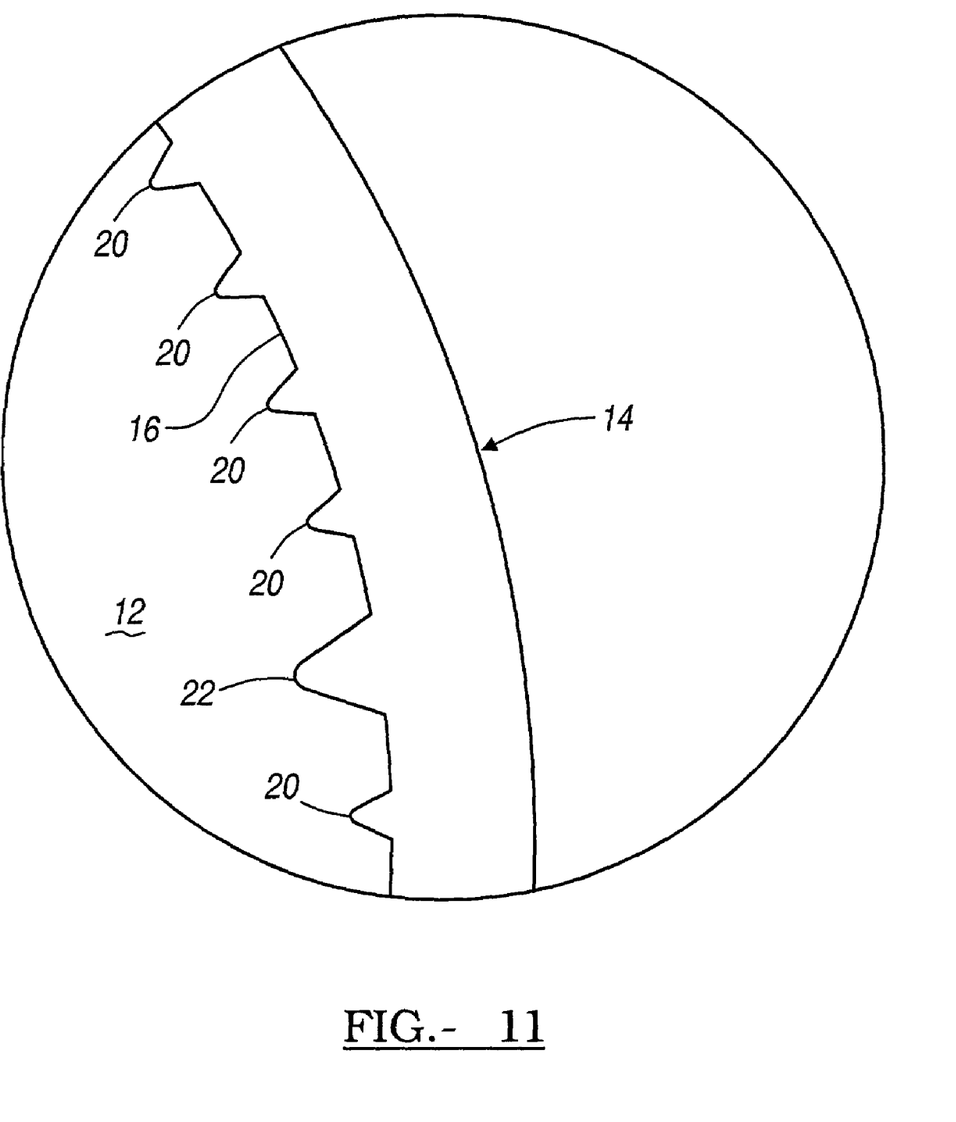
FIG. 11 illustrates a partial detailed view of the interface between the thermoplastic backing and the ceramic liner of the completed composite acetabular component, in accordance with the general teachings of the present invention.

The softened UHMWPE or other thermoplastic material 104 (from softened UHMWPE or other thermoplastic material source 106) is then be brought into contact with the back surface 16 of the ceramic liner 12 for a sufficient period of time so as form a thermoplastic backing 14 on the back surface 16 of the ceramic liner 12. In this manner, the UHMWPE or other thermoplastic material 104 is molded around the ceramic liner 12, especially the back surface 16 thereof. The completed modular acetabular component 10 is then removed from the mold tool 100. The softened UHMWPE or other thermoplastic material 104 preferably penetrates into the textured surface 18 of the back surface (e.g., surface micro-roughness 20 and/or macro-grooves 22) so as to enhance the mechanical bonding of the backing 14 to the ceramic liner 12, as shown in FIG. 11.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. An acetabular liner component, comprising:
   a ceramic insert portion having an inner surface and an outer surface; and a biocompatible thermoplastic backing portion molded onto the outer surface of the ceramic insert portion when the biocompatible thermoplastic backing portion is in a substantially softened state;

a groove formed in an outer surface of said biocompatible thermoplastic backing portion adapted to receive an inter-connection member;

wherein the outer surface of the ceramic insert portion is provided with a micro-roughness having an arithmetical mean roughness in a range of about 5 to about 10 microns and a plurality of longitudinally disposed macro-grooves so as to increase the mechanical bonding between the biocompatible thermoplastic backing portion and the outer surface of the ceramic insert portion.

2. The composite acetabular liner component according to claim 1, wherein the ceramic insert portion has a substantially hemispherical shape.

3. The composite acetabular liner component according to claim 1, wherein the outer surface of the ceramic insert portion comprises a roughened surface.

4. The composite acetabular liner component according to claim 3, wherein the roughened surface has a ten-point mean roughness in a range of about 50 to about 75 microns.

5. The composite acetabular liner component according to claim 1, wherein the biocompatible thermoplastic backing portion has a substantially hemispherical surface, and wherein the macro-grooves are longitudinally oriented with respect to the hemispherical shape.

6. The composite acetabular liner component according to claim 1, wherein the biocompatible thermoplastic backing portion is comprised of polyethylene.

7. The composite acetabular liner component according to claim 1, wherein the biocompatible thermoplastic backing portion is comprised of ultra high molecular weight polyethylene.

8. A composite acetabular liner component, comprising:

a ceramic insert member, the ceramic insert member having a substantially hemispherical shape, the ceramic insert member having an inner surface and an outer surface; and a biocompatible thermoplastic backing member molded onto the outer surface of the ceramic insert member when the biocompatible thermoplastic backing member is in a substantially softened state, the biocompatible thermoplastic backing member having a substantially hemispherical shape, the biocompatible thermoplastic backing member having an inner surface and an outer surface;

a connection system including a groove formed in the outer surface of said biocompatible thermoplastic backing member adapted to receive a locking member;

wherein the outer surface of the ceramic insert is provided with a roughened texture and a plurality of longitudinal macro-grooves so as to increase the mechanical bonding between the inner surface of the biocompatible thermoplastic backing member and the roughened texture of the outer surface of the ceramic liner member.

9. The composite acetabular liner component according to claim 8, wherein the texture comprises a micro-roughened surface.

10. The composite acetabular liner component according to claim 9, wherein the roughened surface has an arithmetical mean roughness in a range of about 5 to about 10 microns.

11. The composite acetabular liner component according to claim 8, wherein the biocompatible thermoplastic backing member is comprised of polyethylene which substantially penetrates into the textured macro-grooves.

12. The composite acetabular liner component according to claim 8, wherein the biocompatible thermoplastic backing member is comprised of ultra high molecular weight polyethylene, and wherein the macro-grooves are substantially radially positioned on the outer surface of the ceramic insert.

13. An acetabulum replacement system, comprising:

an acetabulum member operable to be positioned in an acetabulum;

a composite acetabular liner component, comprising:

a ceramic insert member having an inner surface and an outer surface; and a biocompatible thermoplastic backing member molded onto the outer surface of the ceramic insert member when the biocompatible thermoplastic backing member is in a substantially softened state;

wherein the outer surface of the ceramic insert is provided with micro-roughness and a plurality of longitudinally positioned macro-grooves so as to increase the mechanical bonding between the biocompatible thermoplastic backing member and the outer surface of the ceramic liner member; and a securing member operable to interconnect the acetabulum member and the composite acetabular liner component by fitting interaction with a structure in an outer surface of the biocompatible thermoplastic backing member.

14. The acetabulum replacement system of claim 13, wherein said securing member includes a deflectable ring positionable between said acetabulum member and said composite acetabular component.

15. The acetabulum replacement system of claim 14, at least one of said acetabulum member or said composite acetabular component define a groove to interact with at least a portion of said ring.

16. The acetabulum replacement system of claim 13, wherein said acetabulum member defines a groove on an inside thereof.

17. The acetabulum replacement system of claim 13, wherein said composite acetabular component defines a groove on an exterior thereof.

18. A hip replacement system, comprising:

an acetabulum member;

a composite acetabular component, comprising:

a ceramic insert member having an inner surface and an outer surface; and a biocompatible thermoplastic backing member molded onto the outer surface of the ceramic insert member when the biocompatible thermoplastic backing member is in a substantially softened state;

wherein the outer surface of the ceramic insert is provided with micro-roughness and a plurality of longitudinally oriented macro-grooves so as to increase the mechanical bonding between the biocompatible thermoplastic backing member and the outer surface of the ceramic liner member;

a femoral component having a ball-shaped portion adapted to be received in the composite acetabular component; and a securing member interconnecting the acetabulum member and the composite acetabular component by engaging an outer surface of the biocompatible thermoplastic backing member.

19. A method of making a composite acetabular component, comprising:

providing a ceramic insert member having an inner surface and an outer surface;

providing a biocompatible thermoplastic material;

imparting micro-roughness and a plurality of radially disposed and longitudinally oriented macro-grooves to the outer surface of the ceramic insert member;

softening the biocompatible thermoplastic material;

contacting the outer surface of the ceramic insert member with the softened biocompatible thermoplastic material for a sufficient period of time to form a biocompatible thermoplastic backing member onto the outer surface of the ceramic insert member; and interconnecting the composite acetabular component with an acetabulum implant with an interconnecting member by fitting the interconnecting member in a structure in an outer surface of the biocompatible thermoplastic backing member;

wherein the micro-roughness and a plurality of radially disposed and longitudinally oriented macro-grooves of the outer surface of the ceramic insert member increases the mechanical bonding between the biocompatible thermoplastic backing member and the outer surface of the ceramic liner member.

20. The method according to claim 19, wherein the ceramic insert member has a substantially hemispherical shape.

21. The method according to claim 19, wherein the micro-roughness of a outer surface has an arithmetical mean roughness in a range of about 5 to about 10 microns.

22. The method according to claim 19, wherein the micro-roughness of a outer surface has a ten-point mean roughness in a range of about 50 to about 75 microns.

23. The method according to claim 19, wherein the biocompatible thermoplastic backing member has a substantially hemispherical shape.

24. The method according to claim 19, wherein the biocompatible thermoplastic backing member is comprised of polyethylene.

25. The method according to claim 19, wherein the biocompatible thermoplastic backing member is comprised of ultra high molecular weight polyethylene.

* * * * *